(12) United States Patent  (10) Patent No.: US 8,092,422 B2
Seiferlein et al.  (45) Date of Patent: Jan. 10, 2012

(54) DUAL-CHAMBER CARPULE WITH ATTACHMENT

(75) Inventors: Werner Seiferlein, Frankfurt am Main (DE); Jörn Möckel, Frankfurt am Maim (DE)

(73) Assignee: Sanofi-Aventis Deutschland GmbH (DE)

( * ) Notice: Subject to any disclaimer, the term of this patent is extended or adjusted under 35 U.S.C. 154(b) by 0 days.

(21) Appl. No.: 12/636,963

(22) Filed: Dec. 14, 2009

(65) Prior Publication Data

US 2010/0274186 A1  Oct. 28, 2010

Related U.S. Application Data

(63) Continuation of application No. PCT/EP2008/004355, filed on May 31, 2008.

(30) Foreign Application Priority Data

Jun. 14, 2007 (EP) ..................................... 07011687

(51) Int. Cl.
*A61M 5/19* (2006.01)
(52) U.S. Cl. ......................................................... 604/89
(58) Field of Classification Search .................... 604/82, 604/89, 90, 91
See application file for complete search history.

(56) References Cited

U.S. PATENT DOCUMENTS

| 4,226,236 | A |  | 10/1980 | Genese et al. |
| 5,069,670 | A | * | 12/1991 | Vetter et al. ................... 604/243 |
| 5,788,670 | A |  | 8/1998 | Reinhard et al. |
| 6,544,233 | B1 | * | 4/2003 | Fukui et al. ................... 604/191 |
| 6,645,179 | B1 | * | 11/2003 | Ishikawa et al. .............. 604/181 |
| 2003/0036724 | A1 | * | 2/2003 | Vetter et al. ..................... 604/85 |

FOREIGN PATENT DOCUMENTS

| DE | 4445969 | 3/1996 |
| EP | 0397977 | 11/1990 |
| EP | 0520618 | 12/1992 |
| EP | 0568321 | 11/1993 |
| EP | 1066847 | 1/2001 |
| EP | 1093826 | 4/2001 |
| EP | 1287841 | 3/2003 |
| GB | 705392 | 3/1954 |
| GB | 2010681 | 7/1979 |

* cited by examiner

*Primary Examiner* — Nicholas Lucchesi
*Assistant Examiner* — Aarti B Berdichevsky
(74) *Attorney, Agent, or Firm* — McDonnell Boehnen Hulbert & Berghoff LLP

(57) ABSTRACT

The invention relates to a dual-chamber carpule comprising a cylinder (1) comprising a bypass (3), a central plug (6) and an end plug (10), and an attachment; the invention further relates to a method for producing and filling said dual-chamber carpule.

14 Claims, 7 Drawing Sheets

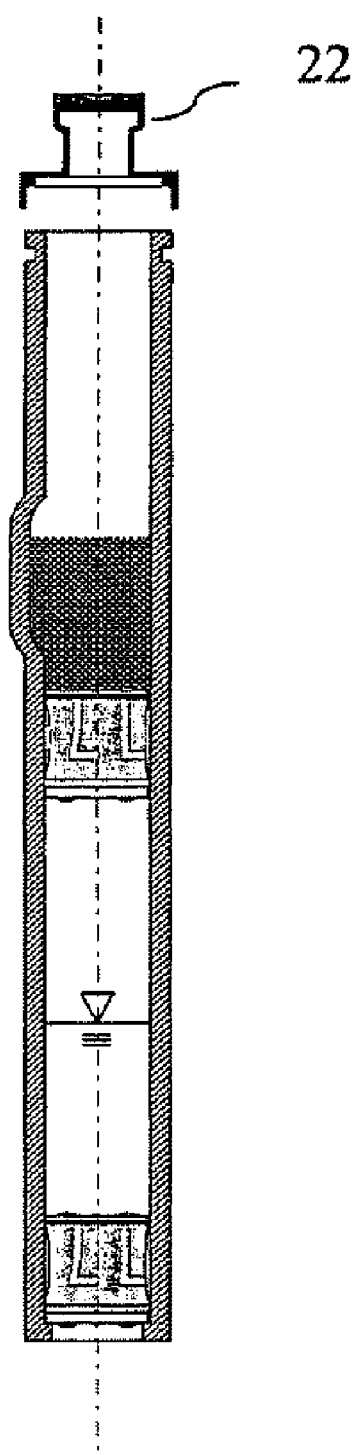
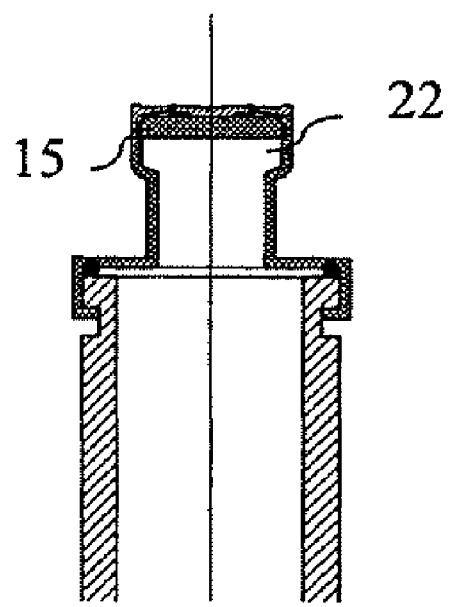
Fig. 3a          Fig. 3b

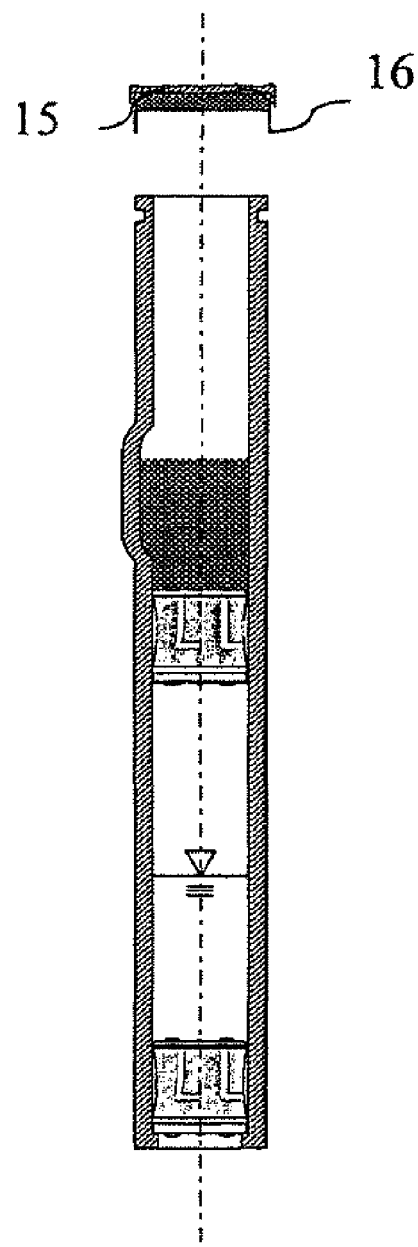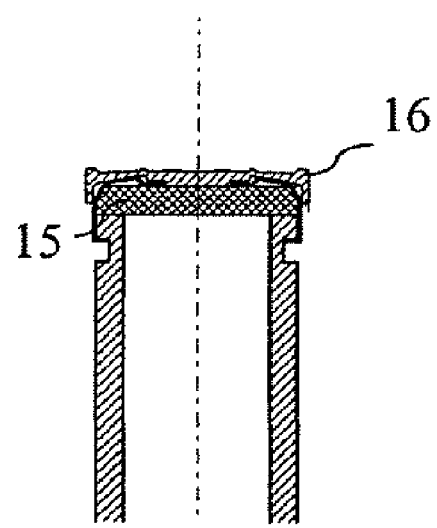
Fig. 4a
Fig. 4b

DUAL-CHAMBER CARPULE WITH ATTACHMENT

This application is a continuation of International application No. PCT/EP2008/004,355, filed May 31, 2008, which is incorporated herein by reference in its entirety; which claims the benefit of priority of European Patent Application No. 07011687.6, filed Jun. 14, 2007.

Two-chamber carpules are used in medicine for administering preparations that comprise two components. There are two possibilities here for combining the components, namely the liquid/liquid combination and the solid/liquid combination. Two-chamber carpules have the advantage that the mixing of the two components can take place without decanting into another container and that administering can then be performed directly from the container. Two-chamber carpules can be used in reusable syringe or pen systems intended for them.

DE 4445969, EP 718002 and U.S. Pat. No. 5,778,670 describe syringe cylinders of two-chamber syringes for two components to be applied, a first part-cylinder, preferably the part-cylinder on the head side, containing an active substance to be lyophilized, and a second part-cylinder, preferably the part-cylinder on the plunger side, containing a liquid component. During administering, the powdered active substance mixes with the liquid component by way of a bypass. The part-cylinder on the needle side contains the bypass and is closed at the proximal end by a plug. The part-cylinder on the head side is closed at the proximal end on the plunger side (FIG. 2) by a plug and optionally at the distal end (FIG. 3) by a further plug. The two part-cylinders are connected to each other by means of material bonding (by welding) or by means of nonpositive engagement (by adhesion). The syringe cylinders described have a bypass, which is preferably formed in such a way that it does not increase the diameter of the syringe cylinder. The material of the front part-cylinder is preferably plastic. In the method for filling the syringe cylinder, the syringe head of the first part-cylinder is closed by a so-called tip cap, i.e. by a loose closure through which the surrounding vacuum can be passed on to the interior of the syringe cylinder in the freeze-drying that follows filling with the active substance to be lyophilized, and which is only securely closed after the freeze-drying step. Separate filling into a first part-cylinder and a second part-cylinder avoids cross contamination and permits optimum utilization of the process space of the lyophilizer.

European patent application EP 520618 describes a pre-filled syringe comprising two part-cylinders, the first part-cylinder, preferably the part-cylinder on the head side, which comprises the needle or the outlet, containing a lyophilized, powdered medicament, and the second part-cylinder, preferably the part-cylinder on the plunger side, containing a second, liquid component. During administering, the powdered medicament mixes with the liquid component by way of a bypass. The part-cylinder on the needle side contains the bypass and is closed at the proximal end by a plug. The part-cylinder on the plunger side is closed at the distal end and at the proximal end by a plug in each case. The two part-cylinders are separately sealed by means of the plugs and connected to each other by means of flanges, the proximal plug of the part-cylinder on the head side and the distal plug of the part-cylinder on the plunger side being positively connected to each other after being joined together, and the overall length of the two plugs being shorter than the length of the bypass.

GB 2010681 describes a two-chamber syringe for administering a liquid comprising two part-cylinders, the first part-cylinder being formed as a needle holder and comprising a channel to the outlet, and the second part-cylinder, on the plunger side, containing liquid. The first part-cylinder does not contain any substance to be administered. During administering, a plunger with which the part-cylinder on the plunger side is closed at the distal end is moved in the direction of the syringe head, whereby the liquid can be applied by way of the channel of the first part-cylinder.

FR 1099362 describes a two-chamber syringe comprising two part-cylinders, the first part-cylinder, on the head side, containing a sterile powder or a sterile liquid and the second part-cylinder, on the plunger side, containing a liquid. During administering, the sterile powder or the sterile liquid of the first part-cylinder mixes with the liquid of the second part-cylinder by way of a bypass in the first part-cylinder, on the needle side. The part-cylinder on the plunger side is closed at the distal end by a plug and at the proximal end by a plunger. The two part-cylinders are connected to each other by adhesion or welding by means of flanges or by means of a further (over) cylinder, the inside diameter of which corresponds to the outside diameter of the two part-cylinders.

The prior-art syringe systems have the disadvantage that they are not suitable for insertion into a syringe applicator (pen or the like) owing to the distal end formed with a needle holder and/or the solid active substance first has to be filled in through a comparatively small opening as a solution or suspension and subsequently has to be lyophilized in the part-cylinder on the needle side in order to obtain a solid, powdered component. Moreover, no solution compensating for the pressure produced when the two part-cylinders are joined together is mentioned in the prior art.

The object of the present invention is therefore to provide an improved two-chamber carpule and an improved method for producing two-chamber carpules and for filling two-chamber carpules.

The present invention relates to a two-chamber carpule comprising
  a) a cylinder containing
    an end plug, which is positioned at the proximal end of the cylinder,
    optionally a stop at the proximal end,
    an intermediate plug,
    a bypass,
    a distal opening for connecting to the attachment,
  b) an attachment comprising
    a closure with a distal opening suitable for piercing with an application needle and optionally a needle holder,
    one or more sealing elements for sealing the distal end of the closure and for sealing the connection between the closure and the cylinder.

A chamber (18) is formed between the end plug and the intermediate plug and a chamber (17) is formed between the intermediate plug and the attachment.

The attachment forms the termination of the cylinder (1) and is attached above the bypass (distally). Preferably, the chamber (17) on the head side is filled with a dry active preparation (12). The plug (6) can move satisfactorily over the join. The cylinder and the closure are connected to each other in a sealed manner.

The cylinder may comprise one or two part-cylinders. The needle holder is a device for receiving a device to which a needle is fastened.

The front chamber (17), which is formed between the intermediate plug (6) and the attachment in the assembled state, contains a solid or liquid component, preferably a solid component, with particular preference a lyophilisate or powder. The rear chamber (18), which is formed between the end plug (10) and the intermediate plug (6) in the assembled state, contains a liquid component. The solid or liquid component of the front chamber and the liquid component of the rear chamber form the medicament to be administered.

The proximal end of the cylinder (1) preferably has a stop (13). The stop prevents slipping of the end plug (10) being caused by the pressure in the direction of the proximal end produced during joining together. The stop is formed in such a way that the plunger of an application system can transfer force to the end plug.

"Proximal" means the end of a component that is facing the end plug (10) in the assembled state, that is to say facing the plunger or the finger actuating the plunger of the person administering the preparation when the two-chamber carpule is installed in a pen system and a plunger of the application system acting on the end plug (10) is actuated by the thumb of the person administering the preparation. The proximal end of the attachment is the end of the head that is connected to the distal end of the cylinder in the assembled state.

"Distal" means the end of a component that is facing the outlet opening in the assembled state.

The "end on the head side of the two-chamber carpule" is the end of the two-chamber carpule that forms the head of the two-chamber carpule, that is to say comprises the outlet opening.

The "end on the plunger side of the two-chamber carpule" is the end of the two-chamber carpule at which the end plug (10) is located and on which the plunger acts in an application system.

Plugs and sealing elements, independently of one another, are made of elastic material, for example rubber, preferably brominated butyl rubber, chlorinated butyl rubber or fluorinated butyl rubber. Optionally, the plugs are coated with PTFE. The plugs are preferably of a cylindrical basic form, but other basic forms corresponding to the inner form of the part-cylinders are also possible. The plugs have both a sealing function and a closing function, for example intermediate plug (6) closes and seals the chamber (18). The sealing function is preferably ensured by one or more lamellar formations of the cylindrical basic form.

"Sealed" means impermeability with respect to solids, liquids, gases and with respect to germs.

The bypass (3) is an opening which makes it possible when the two-chamber carpule is being used for a liquid component (14) to flow out of chamber (18) into chamber (17), bypassing the immediate plug (6), while the medicament is administered. The bypass (3) can be created by one or more channels, which are located in the material of the wall of the part-cylinder (1), i.e. are let into or worked into the material of the wall. By appropriate forming of the material of the wall, the bypass may also be formed inward (not depicted) or outward (as depicted for example in FIG. 1a). The arrangement may be configured axially or radially deviating from the axial direction.

The cylinder and the attachment are formed independently of each other from glass, plastic, metal or other materials, with preference transparent materials such as glass or plastic.

Preferred plastics are polycarbonate, polyesters, cycloolefin copolymers (COO) or cycloolefin polymers (COP).

The medicament contains one or more pharmaceutically active ingredients selected from the group comprising (i) a low molecular weight compound (with a molecular weight of up to 1500 Da), (ii) a peptide, (iii) a protein, (iv) DNA, (v) RNA, (vi) an antibody, (vii) an enzyme and (viii) an oligonucleotide, preferably containing at least one peptide, with preference a peptide for the treatment of Diabetes mellitus or complications of Diabetes mellitus such as for example diabetic retinopathy, with particular preference selected from the group comprising human insulin, a human insulin analog, a human insulin derivative, glucagon-like peptide-1 (GLP1), a GLP1 analog, a GLP1 derivative, exendin-3, exendin-4, an exendin-3 analog, an exendin-4 analog, an exendin-3 derivative or an exendin-4 derivative.

Insulin analogs are, for example, Gly(A21), Arg(B31), Arg (B32) human insulin; Lys (B3), Glu(B29) human insulin; Lys (B28), Pro (B29) human insulin; Asp (B28) human insulin; human insulin in which proline in the position B28 has been substituted by Asp, Lys, Leu, Val or Ala and where Lys in position B29 can be substituted by Pro; Ala (B26) human insulin; des(B28-B30) human insulin; des(B27) human insulin and des(B30) human insulin.

Insulin derivatives are, for example, B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(Ω-carboxyheptadecanoyl)-des(B30) human insulin and B29-N-(ω-carboxyheptadecanoyl) human insulin.

Exendin-4 preferably means exendin-4(1-39), a peptid with the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$.

Exendin-4 derivatives are, for example, selected from the following group of compounds:
H-(Lys)$_4$-des Pro$^{36}$, des Pro$^{37}$ exendin-4(1-39)-$NH_2$,
H-(Lys)$_5$-des Pro$^{36}$, des Pro$^{37}$ exendin-4(1-39)-$NH_2$,
des Pro$^{36}$ [Asp$^{28}$]Exendin-4(1-39),
des Pro$^{36}$ [IsoAsp$^{28}$]exendin-4(1-39),
des Pro$^{36}$ [Met(O)$^{14}$, Asp$^{28}$]exendin-4(1-39),
des Pro$^{36}$ [Met(O)$^{14}$, IsoAsp$^{28}$]exendin-4(1-39),
des Pro$^{36}$ [Trp(O$_2$)$^{25}$, Asp$^{28}$]exendin-4(1-39),
des Pro$^{36}$ [Trp(O$_2$)$^{25}$, IsoAsp$^{28}$]exendin-4(1-39),
des Pro$^{36}$ [Met(O)$^{14}$ Trp(O$_2$)$^{25}$, Asp$^{28}$]exendin-4(1-39),
des Pro$^{36}$ [Met(O)$^{14}$ Trp(O$_2$)$^{25}$, IsoAsp$^{28}$]exendin-4(1-39);
or
des Pro$^{36}$ [Asp$^{28}$]exendin-4(1-39),
des Pro$^{36}$ [IsoAsp$^{28}$]exendin-4(1-39),
des Pro$^{36}$ [Met(O)$^{14}$, Asp$^{28}$]exendin-4(1-39),
des Pro$^{36}$ [Met(O)$^{14}$, IsoAsp$^{28}$]exendin-4(1-39),
des Pro$^{36}$ [Trp(O$_2$)$^{25}$, Asp$^{28}$]exendin-4(1-39),
des Pro$^{36}$ [Trp(O$_2$)$^{25}$, IsoAsp$^{28}$]exendin-4(1-39),
des Pro$^{36}$ [Met(O)$^{14}$ Trp(O$_2$)$^{25}$, Asp$^{28}$]exendin-4(1-39),
des Pro$^{36}$ [Met(O)$^{14}$ Trp(O$_2$)$^{25}$, IsoAsp$^{28}$]exendin-4(1-39),
the group -Lys$_6$-$NH_2$ being linked with the C-terminus of the exendin-4-derivative; or
an exendin-4 derivative of the sequence
H-(Lys)$_6$-des Pro$^{36}$ [Asp$^{28}$]exendin-4(1-39)-Lys$_6$-$NH_2$,
des Asp$^{28}$ Pro$^{36}$, Pro$^{37}$, Pro38exendin-4(1-39)-$NH_2$,
H-(Lys)$_6$-des Pro$^{36}$, Pro$^{38}$ [Asp$^{28}$]exendin-4(1-39)-$NH_2$,
H-Asn-(Glu)$_5$des Pro$^{36}$, Pro$^{37}$, Pro$^{38}$ [Asp$^{28}$]exendin-4(1-39)-$NH_2$,
des Pro$^{36}$, Pro$^{37}$, Pro$^{38}$ [Asp$^{28}$]exendin-4(1-39)-(Lys)$_6$-$NH_2$,
H-(Lys)$_6$-des Pro$^{36}$, Pro$^{37}$, Pro$^{38}$ [Asp$^{28}$]exendin-4(1-39)-(Lys)$_6$-$NH_2$, H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$ [Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Trp(O$_2$)$^{25}$]exendin-4(1-39)-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-NH$_2$,
des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$]exendin-4(1-39)-NH$_2$,
des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$]exendin-4(1-39)-(Lys)$_6$-NH$_2$,
H-Asn-(Glu)$_5$ des Pro$^{36}$, Pro$^{37}$, Pro$^{38}$ [Met(O)$^{14}$, Asp$^{28}$]exendin-4(1-39)-(Lys)$_6$-NH$_2$,
H-Lys$_6$-des Pro$^{36}$ [Met(O)$^{14}$, Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$]exendin-4(1-39)-NH$_2$,
des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$]exendin-4(S1-39)-(Lys)$_6$-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$;
or a pharmaceutically acceptable salt or solvate of exendin-4 or of one of the aforementioned exendin-4 derivatives.

The pharmaceutically active ingredient is preferably the solid component in the chamber of the front part-cylinder, with particular preference a lyophilizate or a powder.

Pharmaceutically acceptable salts are, for example, acid addition salts and basic salts. Acid addition salts are, for example, HCl or HBr addition salts. Basic salts are, for example, salts in which the cation is selected from the group of alkali salts, for example Na$^+$ or K$^+$, or the earth alkali salts, for example Ca$^{2+}$, or ammonia ions N$^+$(R$_1$)(R$_2$)(R$_3$)(R$_4$), where R$_1$ to R$_4$ mean, independently of one another: hydrogen, C$_1$-C$_6$-alkyl, C$_2$-C$_6$-alkenyl, C$_6$-C$_{10}$-aryl, or C$_6$-C$_{10}$-heteroaryl. Further examples of pharmaceutically acceptable salts are described in "Remington's Pharmaceutical Sciences" 17. Ed. Alfonso R. Gennaro (Ed.), Mark Publishing Company, Easton, Pa., U.S.A., 1985 and in Encyclopedia of Pharmaceutical Technology.

The attachment and the cylinder are positively and/or non-positively connected to each other in a way known to a person skilled in the art, for example by screw closure, plug-in closure, bayonet closure, snap-in closure or clamping closure (represented in the figures). Depending on the choice of materials, the connection is with preference self-sealing, or is for example accomplished by adhesion or welding. A sealing element may optionally be used.

In one embodiment, the cylinder (1) is the receiving component. If the head (2) and the cylinder (1) are connected to each other for example by screw closure, the cylinder (1) has an internal thread at the distal end, and the head (2) has a corresponding external thread at the proximal end.

In a further embodiment, the head (2) is the receiving component. If the head (2) and the cylinder (1) are connected to each other for example by screw closure, the head (2) has an internal thread at the proximal end, and the cylinder (1) has a corresponding external thread at the distal end.

In a preferred embodiment, the closure is of a one-piece configuration.

In a particularly preferred embodiment, the closure comprises an integrated closure cap, which may be formed with or without a shoulder. In the case of being formed with a shoulder, with preference the attachment includes a sealing element for sealing the distal end of the integrated closure cap and a further sealing element for sealing the connection between the integrated closure cap and the cylinder. In the case of a cylindrical cross section of the cylinder and the closure, the sealing element is a sealing ring.

It is especially preferred for the attachment to comprise a one-piece, integrated closure cap (22) with a distal opening for attaching onto the cylinder (1) and further comprising a sealing element for sealing the distal end of the integrated closure cap (22) and optionally (with preference) a further sealing element (7) for sealing the connection between the integrated closure cap (22) and the cylinder (1). The integrated closure cap (22) is in this case formed in such a way that slipping of the sealing element in the axial and transverse directions is prevented. The connection between the cylinder and the integrated closure cap takes place with preference by means of a flanging closure, the integrated closure cap engaging in a radial groove at the distal end of the cylinder (1). A further example of a connection is the screw closure.

In a further especially preferred embodiment, the attachment comprises a one-piece closure element (16) characterized by a flanged cap with a distal opening for attaching onto the cylinder (1) and a sealing element (15) for sealing the distal end of the closure element (16) and for sealing the connection between the closure element (16) and the cylinder (1). The closure element (16) is in this case formed in such a way that slipping of the sealing element in the axial and transverse directions is prevented. The connection of the cylinder (1) and the closure element (16) takes place with preference by means of a flanging closure, the closure element (16) engaging in a radial groove at the distal end of the cylinder (1). A further example of a connection is the screw closure.

In a further especially preferred embodiment, the attachment comprises a one-piece closure element (16) with a distal opening, a sealing element (15) for sealing the distal end of the closure element (16) and for sealing the connection between the closure element (16) and the cylinder (1). In this embodiment, the cylinder (1) has a substantially cylindrical basic body and a distal piece which has a diameter that is reduced in comparison with the diameter of the basic body and is provided with a distal opening suitable for piercing with an application needle and optionally a needle holder. For example, the basic body tapers to the piece of reduced diameter by way of a shoulder. The diameter of the distal opening is preferably 6-10 mm, with particular preference 6-9 mm, with special preference 7-9 mm. For example, with an outside diameter of the cylinder (1) of 9-15 mm, the diameter of the distal opening may be 6-9 mm, preferably 6-7 mm. The distal opening ensures easy filling of the carpule with the dry active preparation, in particular with a powder. The closure element (16) is in this case formed in such a way that slipping of the sealing element in the axial and transverse directions is prevented. The connection of the cylinder (1) and the closure element (16) takes place with preference by means of a flanging closure, the closure element (16) engaging the distal end of the piece by means of a bead. A further example of a connection of the cylinder (1) and the closure element (16) is the screw closure.

In a further preferred embodiment, the closure is of a two-piece configuration.

Preferably, the two-piece embodiment includes a sealing element for sealing the distal end of the closure and a further sealing element for sealing the connection between the closure and the cylinder. In the case of a cylindrical cross section of the cylinder and the closure, the sealing element for sealing the connection between the closure and the cylinder is for example a sealing ring. The sealing element for the sealing of the distal end of the closure is with preference a sealing disk.

With particular preference, the closure comprises a head (2) and a closure cap (5). The attachment consequently comprises a head (2) and a closure cap (5) with a distal opening suitable for piercing with an application needle and optionally a needle holder, a sealing element for sealing the connection between the head (2) and the closure cap (5) and optionally a further sealing element (7) for sealing the connection between the head (2) and the cylinder (1). The connection between the cylinder and the head preferably takes place by engagement of the head (2) in the cylinder (1) or by engagement of the cylinder (1) in the head (2). The head (2) has at the proximal end a geometry that is compatible with the distal end of the cylinder (1), for example in the case of a cylindrical basic form of the cylinder (1) a diameter that is compatible with the distal end of the cylinder. The cylinder (1) is with preference of a cylindrical basic form and has with particular preference a diameter that is substantially constant over the entire length. With particular preference, the head and the cylinder are connected to each other by means of clamping closure or, in particular in the case of a cylindrical geometry, by means of screw closure.

In a further preferred embodiment, the closure is of a three-piece configuration.

Preferably, the three-piece embodiment includes a sealing element for sealing the distal end of the closure and a further sealing element for sealing the connection between the closure and the cylinder. In the case of a cylindrical cross section of the cylinder and the closure, the sealing element for sealing the connection between the closure and the cylinder is for example a sealing ring. The sealing element for sealing the distal end of the closure is with preference a sealing disk.

With preference, the closure comprises a head (2), a head holder (19) and a closure cap (5). The attachment consequently comprises a head (2), a head holder (19) and a closure cap (5) with a distal opening suitable for piercing with an application needle and optionally a needle holder, a sealing element for sealing the connection between the head (2) and the closure cap (5) and optionally a further sealing element (7) for sealing the connection between the head (2) and the cylinder (1). The connection between the cylinder and the closure takes place with preference by means of a flanging closure, the head holder (19) engaging in a radial groove at the distal end of the cylinder (1). A further example of a connection is the screw closure. Preferably, a transverse movement of the head with respect to the cylinder is prevented by engagement of the head (2) in the cylinder (1) or by engagement of the cylinder (1) in the head (2).

The closure cap (5) is a device which closes the distal end of the head (2) in a sealed manner. The cap consists of aluminum or a plastic and ensures permanent connection and a sealing force with the head (2). The connection may be established by methods known to a person skilled in the art, for example by crimping, flanging, pressing or screwing.

In an especially preferred embodiment of a two-piece or three-piece closure, either the proximal end of the head (2) or the distal end of the cylinder (1) contains an axial groove (11) on the inner side of the receiving component. When the cylinder (1) and the head (2) are joined together, a pressure which could press out the intermediate plug (6), and possibly also the end plug (10), can build up in the chamber (17). The pressure can be substantially avoided by the axial groove (11), since air can initially escape during joining together. The groove is formed in such a way that it has a length axially that is smaller than the length of the engagement of the proximal end of the engaging component in the corresponding end of the receiving component. Furthermore, the groove is formed in such a way that it further reduces the wall thickness of the receiving component. If, for example, as represented in FIG. 1a, the proximal end of the head (2) engages in the distal end of the cylinder (1), the pressure that is built up during joining together can initially escape through the groove (11). Only in the final assembly step is it no longer possible for the pressure to escape by way of the groove, but the pressure is so low that it can longer change the position of the intermediate plug (6) and the end plug (10). In a particularly preferred embodiment, the cylinder (1) and the head (2), one of which contains an axial groove, are connected to each other by means of clamping closure.

The axial groove (11) may be provided at the proximal end of the head (2) or at the distal end of the cylinder (1); preferably, the axial groove (11) is at the distal end of the cylinder (1). In a preferred embodiment, the two-chamber carpule contains an axial groove (11) in the cylinder (1) and a stop (13) at the proximal end of the cylinder (1).

In a preferred embodiment of a two-piece of three-piece closure, the cylinder (1) and the head (2) are made of plastic. In a particularly preferred embodiment, the two plastic components are connected to each other by means of a screw closure, a sealing element optionally being inserted between the part-cylinders for sealing purposes. It is especially preferred in this embodiment for the distal end of the cylinder (1) to contain an axial groove (11), by way of which the pressure built up in the chamber (17) during the assembly of the two components can escape; alternatively, the intermediate plug (6) and the end plug (10) may be positioned in the cylinder (1) in such a way that, during assembly, both are displaced into the desired end position by the built-up pressure. Preferably, the cylinder (1) contains a stop (13) at the proximal end.

In a further preferred embodiment of a two-piece or three-piece closure, the cylinder (1) consists of glass and the head (2) consists of plastic, which cylinder and head are connected to each other with particular preference by means of a clamping closure.

The sealing of the part-cylinders may take place by adhesion by means of conventional pharmaceutically acceptable adhesive, a sealing element optionally being inserted between the cylinder and the head. It is especially preferred in this embodiment for the distal end of the cylinder (1) to contain an axial groove (11), by way of which the pressure built up in the chamber (17) during the assembly of the two components can escape; alternatively, the intermediate plug (6) and the end plug (10) may be positioned in the cylinder (1) in such a way that, during assembly, both are displaced into the desired end position by the built-up pressure. Preferably, the cylinder (1) contains a stop (13) at the proximal end.

In a further preferred embodiment of a two-piece or three-piece closure, both the cylinder (1) and the head (2) consist of plastic and are connected to each other by means of a plug-in closure, a sealing element optionally being inserted between the part-cylinders for sealing purposes. It is especially preferred in this embodiment for the distal end of the cylinder (1) to contain an axial groove (11), by way of which the pressure built up in the chamber (17) during the assembly of the two components can escape; alternatively, the intermediate plug (6) and the end plug (10) may be positioned in the cylinder (1) in such a way that, during assembly, both are displaced into the desired end position by the built-up pressure. Preferably, the cylinder (1) contains a stop (13) at the proximal end.

The head holder (19) consists for example of metal or plastic, with preference of aluminum.

In general, a combination of all the stated general and preferred features of the embodiments is technically possible.

The following configurational variants are particularly preferred:

1.) The closure is of a two-piece configuration, the material for producing the cylinder (1) and the head (2) is plastic and the connection of the cylinder to the head is brought about by means of a screw closure. The connection is either self-sealing or the sealing of the connection is ensured by means of a sealing element (7) of suitable material.

2.) The closure is of a two-piece configuration, the material for producing the cylinder (1) is glass and the material for producing the head (2) is plastic; connection of the two components (1) and (2) is brought about by means of a clamping closure. The connection is either self-sealing or the sealing of the connection is ensured by means of adhesion with a conventional pharmaceutically acceptable adhesive.

3.) The closure is of a two-piece configuration, the material for producing the cylinder (1) and the head (2) is plastic and the connection of the cylinder to the head is brought about by means of a clamping closure. The connection is either self-sealing or the sealing of the connection is ensured by means of ultrasonic welding.

4.) The closure is of a two-piece configuration, the material for producing the cylinder (1) and the head (2) is glass and the connection of the cylinder to the head is brought about by means of a flanging closure. The sealing of the connection is preferably ensured by means of a sealing element (7) of suitable material.

5.) The closure is of a one-piece configuration, the material for producing the cylinder (1) is glass or plastic and the closure is an integrated closure cap (22) or a one-piece closure element (16) made of metal, with preference aluminum coated with a protective lacquer on the inner side. The connection is preferably additionally ensured by means of a sealing element. The proximal end of the one-piece closure element (16) is crimped with preference with a radial groove (20) at the distal end (8) of the cylinder. If the head is formed as an integrated closure cap (22), the proximal end of the integrated attachment (22) is crimped with preference with a radial groove (20) at the distal end (8) of the cylinder.

6.) The closure is formed as one piece, the material for producing the cylinder (1) has a substantially cylindrical basic body and a distal piece which has a diameter that is reduced in comparison with the diameter of the basic body and is provided with a distal opening suitable for piercing with an application needle and optionally a needle holder, the basic body tapering to the piece of reduced diameter by way of a shoulder. The connection of the cylinder (1) and the closure element (16) takes place by means of a flanging closure or a screw closure.

It is common to all the embodiments that the liquid component (14) and the solid component (12) are filled with preference under sterile conditions.

The two-chamber carpule according to the invention has the advantage that the cylinder can be filled through the entire diameter of the part-cylinders, and that the attachment can be attached after filling of the chamber (17) without risk of contamination by the liquid component (14) at the points of contact between the components. The filling by way of large openings ensures a reduced likelihood of contamination of the other part-cylinder respectively, or the outside of the carpule. Since powder can be filled directly, lyophilizing is not necessary. Instead, a lyophilizate (the product of lyophilization) or some other solid component, preferably in powder form, can be filled in directly. The innocuous filling with powder also ensures that no influencing of the crystalline structure of the powder can occur by way of shearing forces, such as those which can occur during filling through small openings, and so influencing of the biocompatibility of the medicaments to be administered is not to be expected. Furthermore, the location of the separation of the two components, the cylinder and the attachment, is in the region of the chamber (17) on the head side, and so a sterile process can be ensured more easily during powder filling. Fitting the middle plug after filling the chamber (18) on the plunger side rules out any risk of contamination of the two components (12) and (14).

The two-chamber carpule according to the invention can be used in any application system, for example a pen system, the application system preferably including a needle for piercing a distal sealing disk, and a drive mechanism for moving the end plug (10) in the distal direction.

Preferably, the cylinder (1) and the head (2) are injection-molded under clean-room conditions, then sterilized while hermetically packed.

The use of plastic as the material for the part-cylinders additionally ensures low-cost production of the parts, the integration of functional parts required for operating a pen system on one of the part-cylinders (synergies), a simple process to establish freedom from particles, sterilization, depyrogenization, high dimensional stability and recyclability.

The invention also relates to an applicator including a two-chamber carpule as described above.

Further subject matter of the invention is a method for producing and filling a two-chamber carpule, wherein
 a) a cylinder containing a bypass is provided with a middle plug between the bypass and the proximal end;
 b) the chamber between the middle plug and the proximal end is filled with a liquid component;
 c) the chamber containing the liquid component is closed with an end plug;
 d) a liquid component, or with preference solid component, is filled into the chamber between the middle plug and the distal end of the cylinder; and
 e) the distal end of the cylinder is closed with an attachment.

The components of the two-chamber carpule are as defined above in their general and preferred embodiments.

In a preferred embodiment, the middle plug is positioned before the insertion of the end plug in such a way that the built-up pressure displaces the middle plug into the desired end position. The middle plug can in principle be introduced from both ends of the cylinder.

In a further preferred embodiment, the cylinder and the attachment are assembled under vacuum conditions. Displacement of the plugs is substantially avoided by this measure.

A person skilled in the art has at his disposal a series of known possible ways of joining together the cylinder and the attachment. Material-bonding, nonpositively or positively engaging connecting techniques may be used, their suitability depending on the materials that are respectively used for the part-cylinders of the syringe. Suitable for example are: adhesion, welding, clamping closure, screw closure, plug-in closure, bayonet closure, snap-in closure, press-fit closure and flanging closure (=crimping closure). If both part-cylinders are made of plastic, a welded connection comes into consideration in particular; however, adhesion is also possible, a connecting technique that can also be used if both part-cylinders consist of glass. In a further refinement, the two cylinder parts, irrespective of whether they are produced from glass or plastic, may be connected to each other by means of a sealing snap-in connection or include a sealing element. If the closure is of a three-piece construction and, apart from the head (2) and the closure cap (5), includes a head holder (19) as an additional component, the proximal end of the head holder (19) may be crimped with a radial groove (20) at the distal end (8) of the cylinder. If the attachment is formed by a one-piece closure element (16) and a sealing disk (15), the proximal end of the closure element (16) may be crimped with a radial groove (20) at the distal end (8) of the cylinder. If the closure is formed as an integrated closure cap (22), the proximal end of the integrated closure cap (22) may be crimped with a radial groove (20) at the distal end (8) of the cylinder.

BRIEF DESCRIPTION OF THE DRAWINGS

FIG. 2b shows a preassembled head with closure cap (21), upper part.

FIG. 3a shows an integrated closure cap (22), which can be fastened to the cylinder by means of flanging closure (FIG. 3b). FIG. 3b shows the integrated closure cap (22) in the state in which it is connected to the cylinder (crimped).

FIG. 4a shows a closure element (16) and a sealing disk (15) as a one-piece attachment. FIG. 4b shows the one-piece closure element (16) and the sealing disk (15) in the state in which they are connected to the cylinder (crimped).

FIGS. 6a-7d show a method for filling the two-chamber carpule according to the invention. FIG. 6a shows the insertion of the middle plug (6) into the cylinder (1). FIG. 6b shows the filling of the chamber (18) on the plunger side with a liquid carrier medium (14). FIG. 6c shows the closing of the chamber (18) with the end plug (10). FIG. 6d shows the cylinder (1) with the middle plug (6), the end plug (10) and the filled chamber (18) on the plunger side. FIG. 7a shows the cylinder (1) turned for further work to be performed on it, with the middle plug (6), the end plug (10) and the filled chamber (18) on the plunger side, the end on the head side pointing upward. FIG. 7b shows the introduction of the dry active preparation (12). FIG. 7c shows the placing of the head (2), the closure cap (5) and the sealing element (7) on the distal end (8) of the cylinder to obtain the ready-to-use, closed two-chamber carpule.

Figure 1A:
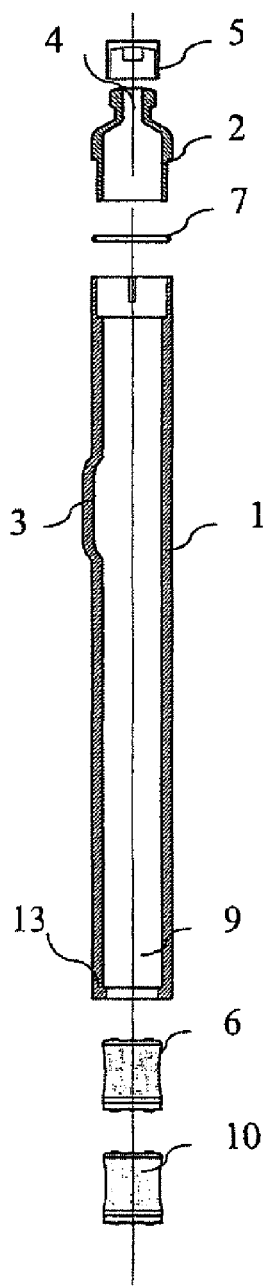
FIGS. 1a and 1b show the basic construction of the invention as an exploded drawing (FIG. 1a) and in the assembled state (FIG. 1b).
Figure 1B:
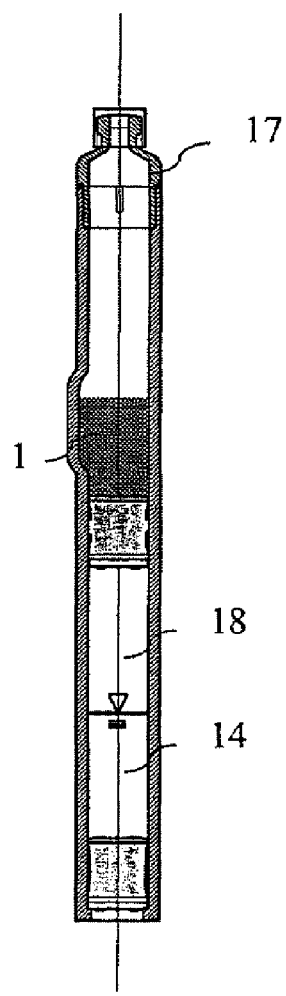
Figure 1C:
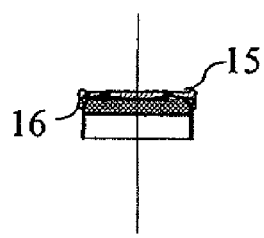
FIG. 1c shows the construction of a closure cap (5). This construction corresponds to the construction of a one-piece closure element.
Figure 2A:
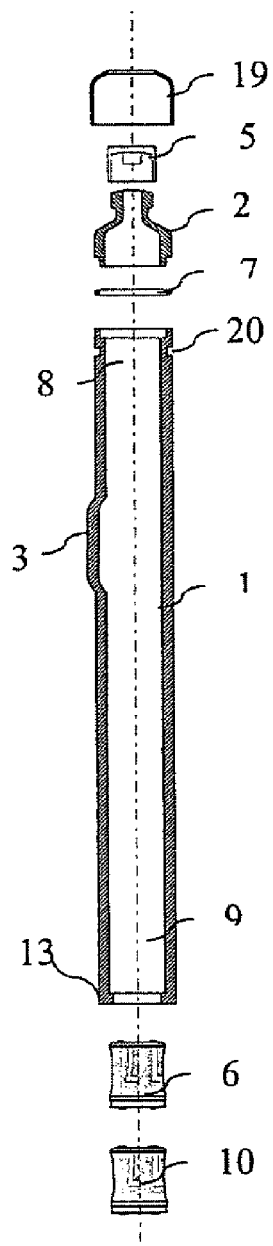
FIGS. 2a to 2c show the connection of the head (2) to the cylinder (1) by means of flanging closure by way of the head holder (19).
Figure 2B:
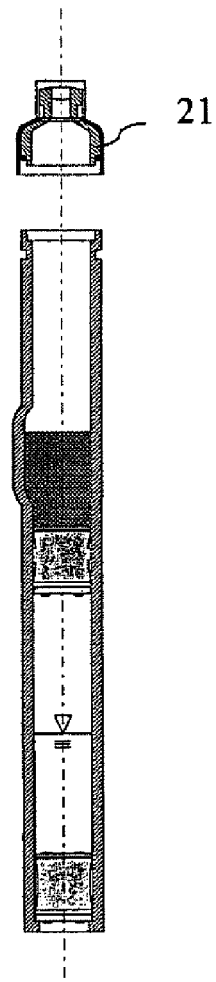
Figure 2C:
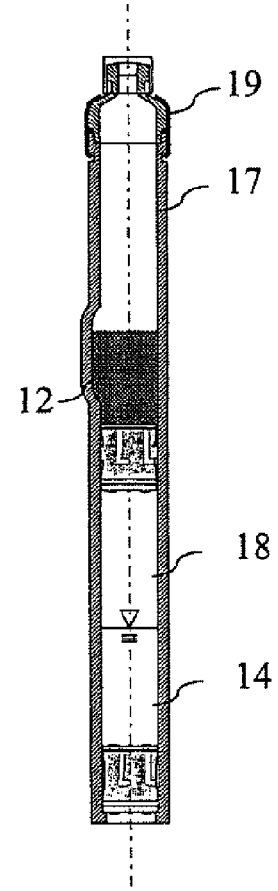
Figure 5:
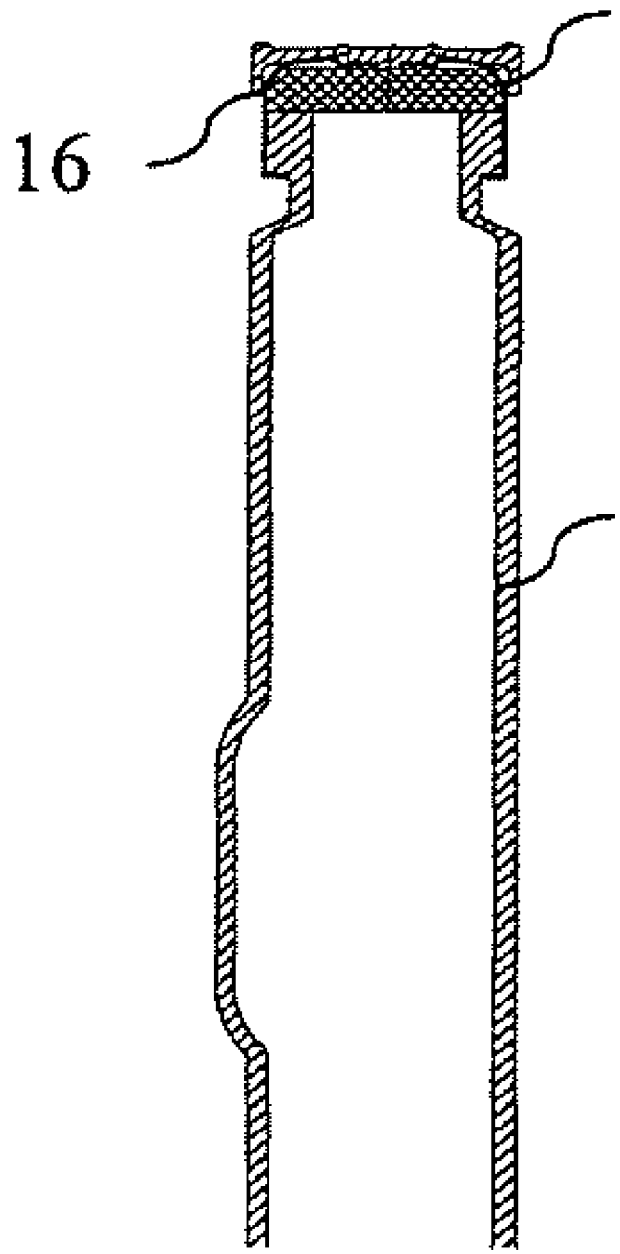
FIG. 5 shows the upper part of a two-chamber carpule with a further embodiment of a one-piece attachment as a closure element (16), a cylinder (1) and a sealing disk (15), the cylinder (1) having a substantially cylindrical basic body and a distal piece which has a diameter that is reduced in comparison with the diameter of the basic body and is provided with a distal opening suitable for piercing with an application needle and optionally a needle holder. The closure element (16) is flanged by means of a bead of the cylinder.
Figures 6A, 6B, 6C, 6D:
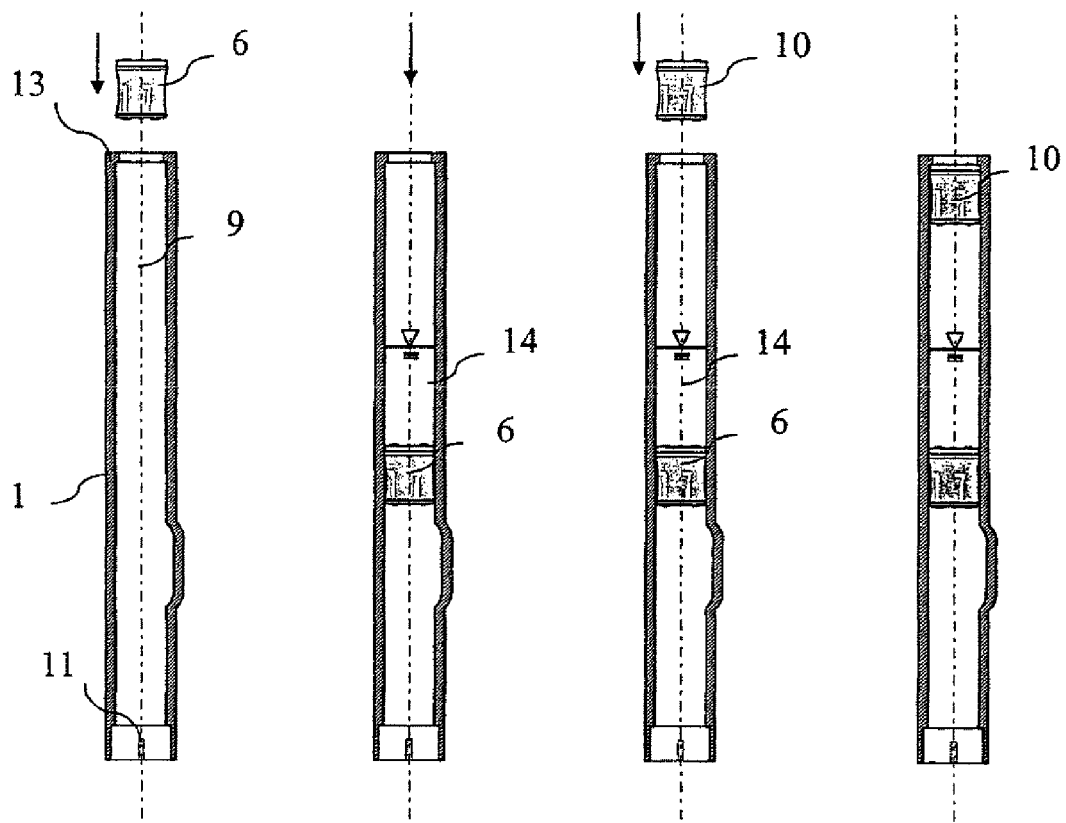
Figures 7A, 7B, 7C, 7D:
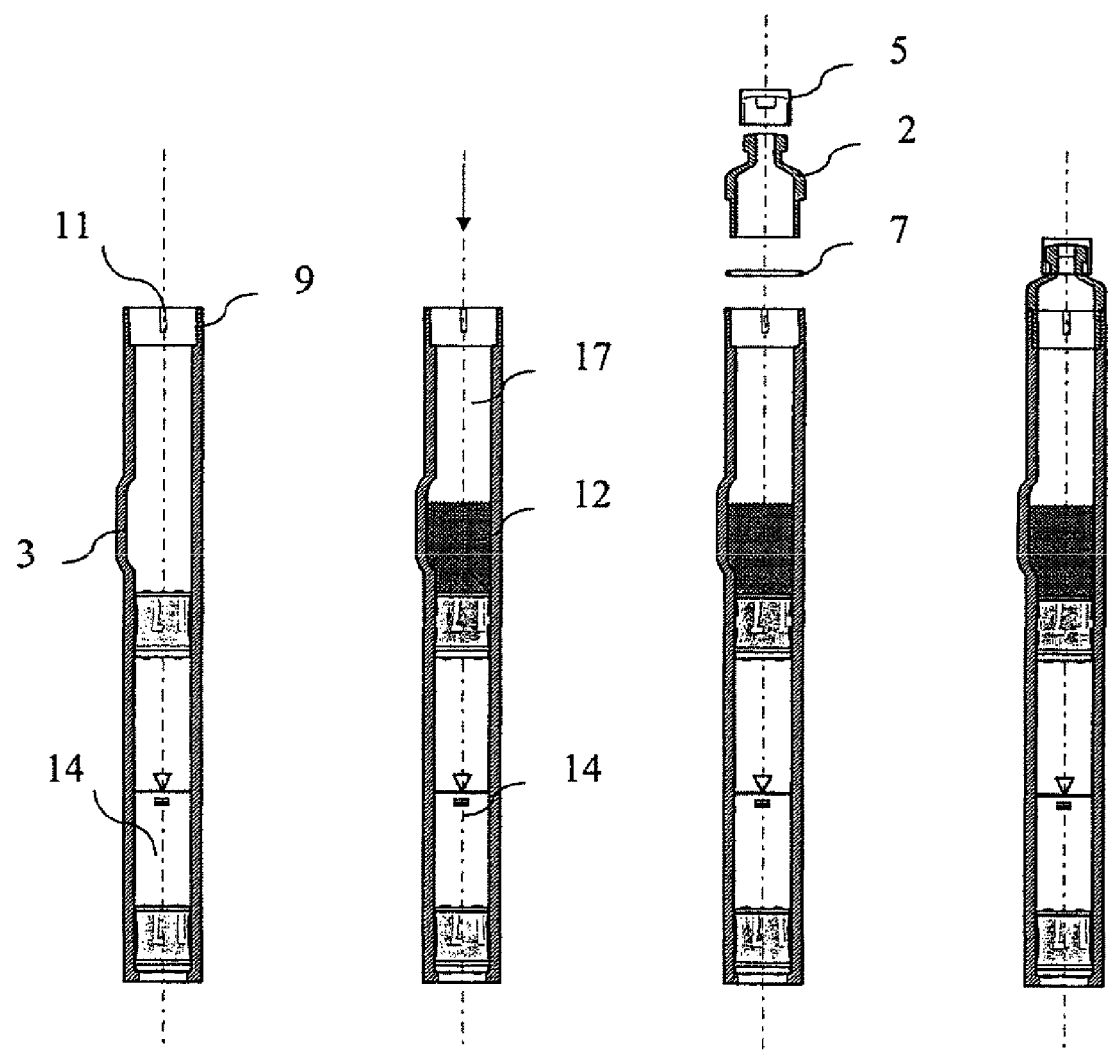

The assembly and filling procedure of the two-chamber carpule is described below by way of example (FIGS. 6-7):
1. Placing of the middle plug (6) into the cylinder (1). The middle plug (6) can be introduced from both ends of the cylinder (1), the preferred end being the proximal end (FIG. 6a).
2. When the middle plug (6) has been brought into its position, the cylinder (1) is filled with liquid carrier medium (14) (FIG. 6b). The size of the chamber (18) is dictated by the volume of the carrier medium (14) to be filled in.
3. When the carrier medium (14) has been filled in, the proximal end (9) of the cylinder is closed with an end plug (10) (FIG. 6c).
4. The cylinder (1) is filled with liquid carrier medium (14) and provided with middle and end plugs is turned by 180°, and so the distal end is pointing upward (FIG. 7a).
5. The cylinder (1) is filled with the dry active preparation (12) (FIG. 7b).
6. The head (2) is attached and connected to the distal end (8) of the cylinder (1) (FIG. 7c). If a sealing element (7) is used, it can be put in place. A closure cap (5) may already be preassembled on the head (2).
7. If the head (2) and the closure cap (5) are not already fitted in a preassembled state in step 6., the closure cap (5) is subsequently placed on the end of the head and connected to the head (2).

If the attachment is of a one-piece configuration, the assembly and filling procedure is carried out as in steps 1.-5., the dry active preparation (12) being filled by way of the distal opening of the cylinder, which is possibly tapered to a piece of reduced diameter, and the closure (16) is subsequently connected to the cylinder (1).

GLOSSARY (1) cylinder
(2) head
(3) bypass
(4) opening
(5) closure cap
(6) middle plug
(7) sealing element
(8) distal end
(9) proximal end
(10) end plug
(11) axial groove
(12) dry active preparation
(13) stop
(14) liquid carrier medium
(15) sealing disk
(16) closure element
(17) chamber on head side
(18) chamber on plunger side
(19) head holder
(20) radial groove
(21) preassembled head with closure cap
(22) integrated closure cap with flanging device

What is claimed is:

1. A two-chamber carpule for use with a pen system comprising
   a) a cylinder having a proximal end and a distal end, containing
      an end plug, which is positioned at the proximal end of the cylinder, optionally a stop at the proximal end,
      an intermediate plug,
      a bypass,
      where the distal end is configured to connect to an attachment, the attachment having a proximal end and a distal end, where the attachment comprises,
      a closure with a distal opening suitable for receiving an application needle and optionally a needle holder,
      one or more sealing elements for sealing the distal opening of the closure and for sealing the connection between the closure and the cylinder; and
   b) an axial groove on an inner side of a receiving component of either the distal end of the cylinder or the proximal end of the attachment, where the axial groove is configured to allow pressure to escape when the cylinder and the attachment are joined together during assembly,
   wherein the cylinder and the attachment when in an assembled state contains a preparation and is configured to be inserted and installed into a pen system.

2. The two-chamber carpule as claimed in claim 1, the closure being of a one-piece configuration.

3. The two-chamber carpule as claimed in claim 2, the closure being formed by an integrated closure cap with or without a head part.

4. The two-chamber carpule as claimed in claim 2, the attachment comprising a one-piece, integrated closure cap with a distal opening, a sealing element for sealing the distal end of the integrated closure cap and optionally (with preference) a further sealing element for sealing the connection between the integrated closure and the cylinder.

5. The two-chamber carpule as claimed in claim 2, the attachment comprising a one-piece closure element with a distal opening, a sealing element for sealing the distal end of the closure element and for sealing the connection between the closure element and the cylinder.

6. The two-chamber carpule as claimed in claim 1, the closure being of a two-piece configuration.

7. The two-chamber carpule as claimed in claim 6, the attachment comprising a head and a closure cap with a distal opening suitable for piercing with an application needle and optionally a needle holder, a sealing element for sealing the connection between the head and the closure cap and optionally a further sealing element for sealing the connection between the head and the cylinder.

8. The two-chamber carpule as claimed in claim 6, the proximal end of the head or the distal end of the cylinder having an axial groove on the inner side of the receiving component, and the proximal end of the cylinder having a stop.

9. The two-chamber carpule as claimed in claim 1, the closure being of a three-piece configuration.

10. The two-chamber carpule cartridge as claimed in claim 9, the attachment comprising a head, a head holder and a closure cap with a distal opening suitable for piercing with an application needle and optionally a needle holder, a sealing element for sealing the connection between the head and the closure cap and optionally a further sealing element for sealing the connection between the head and the cylinder.

11. The two-chamber carpule as claimed in claim 1, a medicament to the administered being a peptide for the treatment of Diabetes mellitus or complications of Diabetes mellitus.

12. The two-chamber carpule as claimed in claim 11, the peptide being exendin-4(1-39) or a peptide selected from the group comprising
H-(Lys)$_4$-des Pro$^{36}$, des Pro$^{37}$ exendin-4(1-39)-NH$_2$,
H-(Lys)$_5$-des Pro$^{36}$, des Pro$^{37}$ exendin-4(1-39)-NH$_2$,
des Pro$^{36}$ [Asp$^{28}$]exendin-4(1-39),
des Pro$^{36}$ [IsoAsp$^{28}$]exendin-4(1-39),
des Pro$^{36}$ [Met(O)$^{14}$, Asp$^{28}$]exendin-4(1-39),
des Pro$^{36}$ [Met(O)$^{14}$, IsoAsp$^{28}$]exendin-4(1-39),
des Pro$^{36}$ [Trp(O$_2$)$^{25}$, Asp$^{28}$]exendin-4(1-39),
des Pro$^{36}$ [Trp(O$_2$)$^{25}$, IsoAsp$^{28}$]exendin-4(1-39),
des Pro$^{36}$ [Met(O)$^{14}$ Trp(O$_2$)$^{25}$, Asp$^{28}$]exendin-4(1-39),
des Pro$^{36}$ [Met(O)$^{14}$ Trp(O$_2$)$^{25}$, IsoAsp$^{28}$]exendin-4(1-39), H—
(Lys)$_6$-des Pro$^{36}$ [Asp$^{28}$]exendin-4(1-39)-Lys6-NH$_2$,
des Asp$^{28}$ Pro$^{36}$, Pro$^{37}$, Pro$^{38}$ exendin-4(1-39)-NH$_2$,
H-(Lys)$_6$-des Pro$^{36}$, Pro$^{38}$ [Asp$^{28}$]exendin-4(1-39)-NH$_2$,
H-Asn-(Glu)$_5$des Pro$^{36}$, Pro$^{37}$, Pro$^{38}$ [Asp$^{28}$]exendin-4(1-39)-NH$_2$,
des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$, Pro$^{37}$, Pro$^{38}$ [Asp$^{28}$]exendin-4(1-39)-(Lys)6-NH$_2$,
H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$ [Trp(O$_2$)$^{25}$, Asp$^{28}$]exendin-4(1-39)-Lys6-NH$_2$,
H-des Asp$^{28}$ Pro$^{36}$, Pro$^{37}$, Pro$^{38}$ [Trp(O$_2$)$^{25}$]exendin-4(1-39)-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-NH$_2$, H-Asn-
(Glu)$_5$-des Pro$^{36}$, Pro$^{37}$, Pro$^{38}$ [Trp(O$_2$)$^{25}$, Asp$^{28}$]exendin-4(1-39)-NH$_2$,
des Pro$^{36}$, Pro$^{37}$, Pro$^{38}$ [Trp(O$_2$)$^{25}$, Asp$^{28}$]exendin-4(1-39)-(Lys)6-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$] exendin-4(1-39)-(Lys)6-NH$_2$, H—
(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$,
des Pro$^{36}$, Pro$^{37}$, Pro$^{38}$ [Met(O)$^{14}$, Asp$^{28}$]exendin-4(1-39)-(Lys)6-NH$_2$,
H-(Lys)$_6$-des Pro$^{36}$, Pro$^{37}$, Pro$^{38}$ [Met(O)$^{14}$, Asp$^{28}$]exendin-4(1-39)-(Lys)$_6$-NH$_2$,
H-Asn-(Glu)$_5$ des Pro$^{36}$, Pro$^{37}$, Pro$^{38}$ [Met(O)$^{14}$, Asp$^{28}$] exendin-4(1-39)-(Lys)$_6$-NH$_2$, H—
Lys$_6$-des Pro$^{36}$ [Met(O)$^{14}$, Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$]exendin-4(1-39)-NH$_2$,
des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$, H-$(Lys)_6$-des $Pro^{36}$, $Pro^{37}$, $Pro^{38}$ [$Met(O)^{14}$, $Trp(O_2)^{25}$, $Asp^{28}$]exendin-4(S1-39)-$(Lys)_6$-$NH_2$, H-Asn-$(Glu)_5$-des $Pro^{36}$, $Pro^{37}$, $Pro^{38}$ [$Met(O)^{14}$, $Trp(O_2)^{25}$, $Asp^{28}$]exendin-4(1-39)-$(Lys)_6$-$NH_2$; or des $Pro^{36}$ [$Asp^{28}$]exendin-4(1-39), des $Pro^{36}$ [$IsoAsp^{28}$]exendin-4(1-39), des $Pro^{36}$ [$Met(O)^{14}$, $Asp^{28}$]exendin-4(1-39), des $Pro^{36}$ [$Met(O)^{14}$, $IsoAsp^{28}$]exendin-4(1-39), des $Pro^{36}$ [$Trp(O_2)^{25}$, $Asp^{28}$]exendin-4(1-39), des $Pro^{36}$ [$Trp(O_2)^{25}$, $IsoAsp^{28}$]exendin-4(1-39), des $Pro^{36}$ [$Met(O)^{14}$ $Trp(O_2)^{25}$, $Asp^{28}$]exendin-4(1-39), des $Pro^{36}$ [$Met(O)^{14}$ $Trp(O_2)^{25}$, $IsoAsp^{28}$]exendin-4(1-39), the group -$Lys_6$-$NH_2$ being linked with the C-terminus of the exendin-4 derivative; or a pharmaceutically acceptable salt or solvate thereof.

13. An applicator including a two-chamber carpule as claimed in claim 1.

14. A method for producing and filling the two-chamber carpule as claimed in claim 1, wherein a) the cylinder containing the bypass is provided with the intermediate plug between the bypass and the proximal end;

b) the chamber between the intermediate plug and the proximal end is filled with a liquid component;

c) the chamber containing the liquid component is closed with the end plug;

d) a liquid component, or with preference solid component, is filled into the chamber between the intermediate plug and the distal end of the cylinder; and e) the distal end of the cylinder is closed with the attachment.

* * * * *